(12) United States Patent
Liu et al.

(10) Patent No.: US 11,193,865 B1
(45) Date of Patent: Dec. 7, 2021

(54) P-Y CURVE-BASED ELEMENT TEST DEVICE AND TEST METHOD

(71) Applicant: QINGDAO UNIVERSITY OF TECHNOLOGY, Qingdao (CN)

(72) Inventors: Junwei Liu, Qingdao (CN); Dongsheng Zheng, Qingdao (CN); Xiuxia Yu, Qingdao (CN); Xianzhang Ling, Qingdao (CN); Lingyun Feng, Qingdao (CN); Shuiyue Chen, Qingdao (CN); Zhipeng Wan, Qingdao (CN); Jianwei Chen, Qingdao (CN); Ning Jia, Qingdao (CN); Hongfeng Guang, Qingdao (CN); Kaiyue Sun, Qingdao (CN); Xu Lv, Qingdao (CN); Changguan Wu, Qingdao (CN); Wei Lv, Qingdao (CN)

(73) Assignee: QINGDAO UNIVERSITY OF TECHNOLOGY, Qingdao (CN)

( * ) Notice: Subject to any disclaimer, the term of this patent is extended or adjusted under 35 U.S.C. 154(b) by 0 days.

(21) Appl. No.: 17/241,097

(22) Filed: Apr. 27, 2021

(30) Foreign Application Priority Data

May 21, 2020 (CN) .......................... 202010434837.2

(51) Int. Cl.
 *G01N 3/16* (2006.01)
 *E02D 33/00* (2006.01)
(52) U.S. Cl.
 CPC .............. *G01N 3/165* (2013.01); *E02D 33/00* (2013.01)

(58) Field of Classification Search
 CPC . G01N 3/00; G01N 3/16; G01N 3/165; E02D 33/00
 See application file for complete search history.

(56) References Cited

U.S. PATENT DOCUMENTS

| 4,885,941 A | * | 12/1989 | Vardoulakis | ............. G01N 3/08 73/794 |
| 10,907,320 B2 | * | 2/2021 | Tan | .......................... E02D 33/00 |
| 2006/0021446 A1 | * | 2/2006 | England | .................. E02D 33/00 73/784 |

\* cited by examiner

*Primary Examiner* — Erika J Villaluna
(74) *Attorney, Agent, or Firm* — Bayramoglu Law Offices LLC

(57) ABSTRACT

A p-y curve-based element test device is provided. An upper support plate is located above a lower support plate and is fixedly connected to the lower support plate through truss supports symmetrically arranged on left and right sides, and at least one truss support is arranged on each side. A sample container, a servo consolidation mechanism and multidirectional servo actuators are connected to the truss support on the two sides. The servo consolidation mechanism is located above the sample container, and the multidirectional servo actuators are arranged above the servo consolidation mechanism and below the sample container, respectively. Identical loads are synchronously applied from above and below to realize horizontal movement of a pile element to simulate the load condition of a soil body, and a pressure is applied by a servo consolidation device to simulate the stress condition of the soil body at a certain depth.

9 Claims, 4 Drawing Sheets

P-Y CURVE-BASED ELEMENT TEST DEVICE AND TEST METHOD

CROSS REFERENCE TO THE RELATED APPLICATIONS

This application is based upon and claims priority to Chinese Patent Application No. 202010434837.2, filed on May 21, 2020, the entire contents of which are incorporated herein by reference.

TECHNICAL FIELD

The invention relates to the field of tests for analyzing horizontal stress characteristics of single pile foundations, in particular to a p-y curve-based element test device and a test method.

BACKGROUND

Offshore wind energy plays an important role in the transformation process to low-carbon energy supply and has developed rapidly in the past ten years. Most offshore wind turbines are constructed based on large-diameter single piles. Single pile foundations are simple in structure and explicit in stress, occupy a small area of the seabed, do not need to be sorted in the early stage, and have the characteristics of high bearing capacity and small and uniform settlement. The pile foundation for offshore wind power mainly withstands horizontal cyclic loads such as winds transmitted from the upper structure, tides and waves rather than vertical loads, all these horizontal loads are low in frequency and cyclic for a long time, and long-term and low-frequency cyclic lateral loads will cause permanent lateral deformation of the single pile foundations. At present, the p-y curve method is widely used for analyzing the horizontal stress characteristics of the single pile foundations for offshore wind power.

At present, most indoor model tests for studying the p-y curve are model batter pile tests and typically simulate the stress response of a whole pile, that is, soil is added into a test box, then a model pile is inserted into the soil, and after that, a horizontal load is applied to the end of the pile to measure the p-y dynamic response at different depths of the pile. All these tests have the following problems: ① the stress field of a soil body on the field is not simulated, so that there will be a large error during field application of a measured p-y curve; ② most tests cannot realize cyclic loading in multiple directions, so there are very few studies on three-dimensional p-y curves at present; and ③ only the p-y curve of a soil layer a certain depth below the earth surface can be obtained, and it is impossible to accurately obtain the p-y curve at any depths of the seabed.

SUMMARY

The objective of the invention is to overcome the above-mentioned defects of the prior art by providing a p-y curve-based element test device, and a test method. According to the p-y curve-based element test device and the test method, identical loads are synchronously applied from above and below to realize horizontal movement of a pile element to simulate the load condition of a soil body, and a pressure is applied by a servo consolidation device to simulate the stress condition of the soil body at a certain depth, such that a p-y response curve at any depths below the earth surface can be accurately obtained.

According to the technical solution of the invention, a p-y curve-based element test device comprises a truss, a sample container, a servo consolidation mechanism and multidirectional servo actuators, wherein the truss comprises an upper support plate, a lower support plate and truss supports, the upper support plate is located above the lower support plate and is fixedly connected to the lower support plate through the truss supports symmetrically arranged on left and right sides, at least one truss support is arranged on each side, the sample container, the servo consolidation mechanism and the multidirectional servo actuators are respectively connected to the truss supports on the two sides, the servo consolidation mechanism is located above the sample container, and the multidirectional servo actuators are arranged above the servo consolidation mechanism and below the sample container, respectively;

The sample container comprises an inner container, an outer container, a top cover plate, a bottom cover plate and a pile element, wherein the inner container contains a rock-soil sample and is located in the outer container, the outer container is connected to the truss through a fixing ring and truss gusset plates, the top cover plate is arranged at the top of the sample container, the bottom cover plate is arranged at the bottom of the sample container, the top cover plate is fixedly connected to the servo consolidation mechanism, the bottom cover plate is located below the fixing ring and is fixedly connected to the fixing ring through a plurality of spring latches;

Porous filter plates are arranged above and below the rock-soil sample in the inner container, the pile element penetrates through a center of the sample container, circular holes are formed in the center of the top cover plate, the center of each porous filter plate and the center of the bottom cover plate correspondingly, the diameter of the circular holes is greater than that of the pile element, partition plates are arranged between the porous filter plates and the rock-soil sample and are disposed around the pile element, and the outer diameter of the partition plates is greater than the diameter of the circular hole in the center of the porous filter plates;

The servo consolidation mechanism comprises two servo motors I symmetrically arranged left and right and two pressure transmission sliders fixedly connected to output ends of the servo motors I, top ends of the servo motors I are fixedly connected to the upper support plate, one end of each pressure transmission slider is fixedly connected to the bottom of one servo motor I, the bottom of the other end of each pressure transmission slider is fixedly connected to the top cover plate, and the pressure transmission sliders are disposed around the truss supports;

The multidirectional servo actuators are mounted at the top and the bottom of the pile element, respectively, and each multidirectional servo actuator comprises a servo motor II, a gear disk and two pinions engaged with the gear disk and arranged symmetrically, wherein the servo motor II is fixed on the gear disk, the two pinions are located on the outer side of the gear disk and are arranged on support plates respectively, central spindles of the pinions are connected to output shafts of motors, and the motors and the support plates are connected to the truss supports through truss gusset plates, respectively.

In the invention, each truss gusset plate comprises a connecting plate, connecting rings and fixing sleeves, wherein two ends of the connecting plate are fixedly connected to the connecting rings, respectively, the connecting rings are cylindrical, the fixing sleeves are fixed in the connecting rings, the connecting plate is fixedly connected to the fixing rings/motors/support plates, and the fixing sleeves are disposed around outer surfaces of the truss supports and are fixedly connected to the truss supports by tightening bolts. When the positions of the truss gusset plates need to be adjusted, the bolts are loosened to allow the truss gusset plates to move vertically along the truss supports, and the fixing sleeves have a guide effect in the moving process.

The inner container is a cylindrical barrel, the outer container is a special-shaped barrel with the size of an outer surface of an upper portion being greater than that of an outer surface of a lower portion, and a step is formed by the variation of an outer diameter of the outer container;

The middle of the outer container is connected to the truss supports through fixing rings II and truss gusset plates, the two fixing rings II are symmetrically arranged in the middle of an outer surface of the outer container, and each fixing ring II has an end formed with an arc opening which clamps the outer surface of the outer container and an end fixedly connected to one truss gusset plate;

A fixing ring I is arranged on the step formed by the variation of the outer diameter of the outer container, is clamped on a lower portion of the outer surface of the outer container, and is circular and closed, the two truss gusset plates are symmetrically arranged on the outer side of the fixing ring I, and the fixing ring I is fixedly connected to the truss gusset plates;

The truss gusset plates are disposed around the truss supports, and positions of the truss gusset plates on the truss supports can be adjusted.

Each pressure transmission slider comprises a connecting block, a truss gusset plate and a pressing block, connecting plates of the truss gusset plates are fixedly connected to the pressing blocks, the pressing blocks are strip-shaped steel blocks, the top cover plate is fixedly connected to bottom surfaces of the two pressing blocks, fixing sleeves of the truss gusset plates are fixedly disposed around the truss supports, connecting rings of the truss gusset plates are fixedly connected to the connecting blocks, and the connecting blocks are fixedly connected to output ends of the servo motors I.

The p-y curve-based element test device further comprises a computer console, wherein a computer system is installed in the computer console and is connected to the servo motors I, the servo motors II and the motors.

The truss supports are hollow pipe supports, and connecting lines between the computer system and the servo motors I, the servo motors II and the motors are arranged in hollow pipes of the truss supports.

The invention further provides a test method using the p-y curve-based element test device, wherein the test method comprises the following steps:

S1: carrying out field sampling: the inner container is used as a rock-soil sampler to carry out field sampling together with a self-made sampler; after sampling is finished, the inner container containing a rock-soil sample is placed back into the outer container; a height of the sample container is adjusted, and then the sample container is fixed;

S2: applying a vertical consolidation pressure: the computer system controls the servo consolidation mechanism to apply a required vertical consolidation pressure downwards, a pressure sensor mounted at a top of the soil sample monitors the pressure in real time and feeds the monitored pressure back to the computer system;

S3: implanting a pile element: the rock-soil sample is consolidated for 2-3 days, and when the stress condition of a soil body becomes stable, the pile element is directly pressed into the rock-soil sample via a pile pressing hole or is implanted into the rock-soil sample by mechanical drilling; and S4: carrying out cyclic loading on the pile element: after the pile element is implanted, a consolidation pressure is maintained and stabilized for 24 hrs, then the computer system controls the multidirectional servo actuators to carry out cyclic loading, and a load-displacement time travel curve is recorded in real time to obtain a p-y curve.

The multidirectional servo actuators apply a monotonic load, a bidirectional horizontal cyclic load or a multi-degree-of-freedom cyclic load; when the gear disks do not rotate, the two servo motors II synchronously apply a load given by the computer system to the top and the bottom of the pile element, and at this moment, the multidirectional servo actuators apply the monotonic load; when a load is applied and released by the two servo motors II in one direction, the computer system controls the pinions to rotate to drive the gear disks to rotate by 180°, then another load is applied and released again, and at this moment, the multidirectional servo actuators apply the bidirectional horizontal cyclic load; and after the servo motors II apply a load in one direction to the pile element, the gear disks are rotated to enable the servo motors II to apply a load in another direction, and at this moment, the multidirectional servo actuators apply the multi-degree-of-freedom cyclic load.

The invention has the following beneficial effects:

Identical loads are synchronously applied from above and below to realize horizontal movement of a pile element to simulate the load condition of a soil body, and a pressure is applied by a servo consolidation device to simulate the stress condition of the soil body at a certain depth, such that a p-y response curve at any depths below the earth surface can be accurately obtained. The device can analyze the dynamic response characteristics of a rock/soil body at different depths of a seabed and provide some suggestions for the design and installation of single pile foundations of offshore wind turbines.

In the figures: 1. inner container; 2. outer container; 3. fixing ring I; 4. fixing ring II; 5. truss gusset plate; 501. connecting plate; 502. connecting ring; 503. fixing sleeve; 6. porous filter plate; 8. pile element; 9. partition plate; 10. bottom cover plate; 11. spring latch; 12. servo motor I; 14. top cover plate; 15. computer console; 16. truss support; 17. upper support plate; 18. pile pressing hole; 19. servo motor II; 20. gear disk; 21. pinion; 22. motor; 23. pressure transmission slider; 2301. connecting block; 2302. truss gusset plate I; 2303. pressing block; 24. lower support plate.

DETAILED DESCRIPTION OF THE EMBODIMENTS

To make the purposes, features and advantages of the invention clearer, specific implementations of the invention will be explained in detail below in conjunction with the accompanying drawings.

Specific details are expounded in the following description to gain a comprehensive understanding of the invention. Obviously, the invention can also be implemented in other manners different from those described herein, and those skilled in the art can make similar generalizations without going against the conception of the invention. Therefore, the invention will not be limited by the specific implementations disclosed below.

Figure 1:
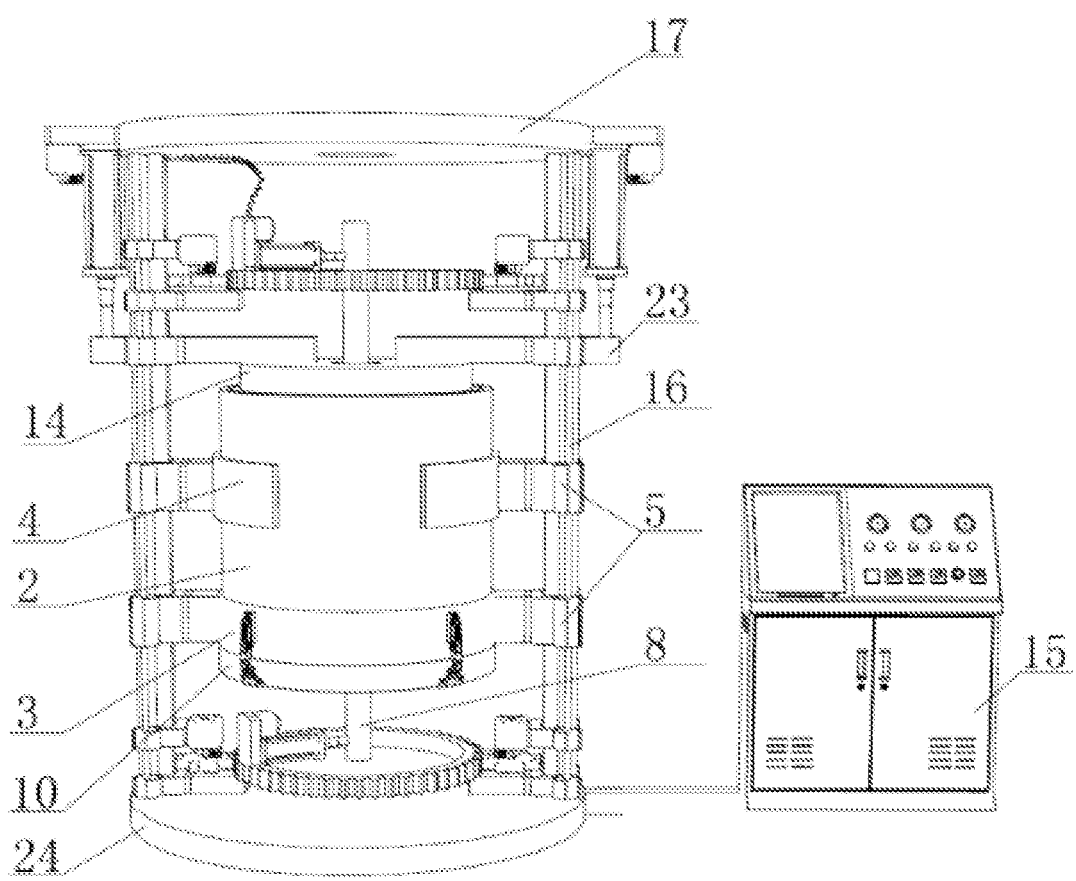
FIG. 1 is a structural diagram of the invention.

As shown in FIG. 1, the invention provides a p-y curve-based element test device which comprises a truss, a sample container, a servo consolidation mechanism, multidirectional servo actuators and a computer console 15. The truss comprises an upper support plate 17, a lower support plate 24 and truss supports 16, wherein the upper support plate 17 is located above the lower support plate 24 and is fixedly connected to the lower support plate 24 through the truss supports 16 which are symmetrically arranged on left and right sides, and at least one truss support 16 is arranged on each side. The sample container, the servo consolidation mechanism and the multidirectional servo actuators are all arranged on the truss and are respectively connected to the truss supports 16 on the two sides, the servo consolidation mechanism is located above the sample container, and the multidirectional servo actuators are arranged above the servo consolidation mechanism and below the sample container, respectively.

Figure 2:
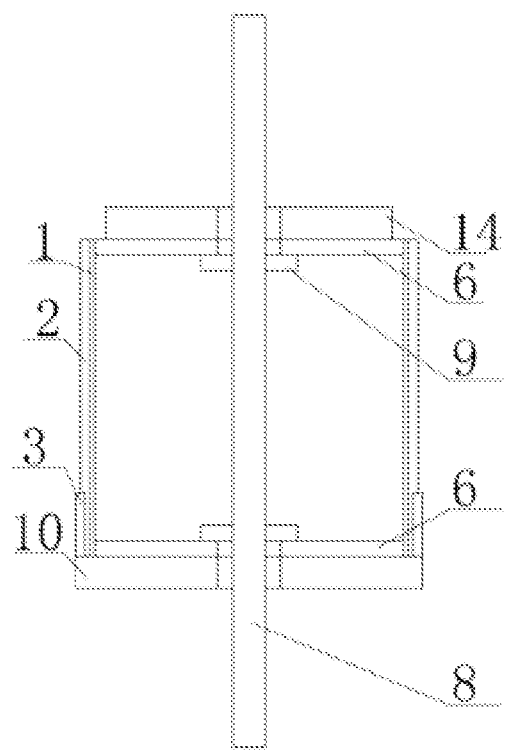
FIG. 2 is a sectional view of a sample container according to the invention.
Figure 3:
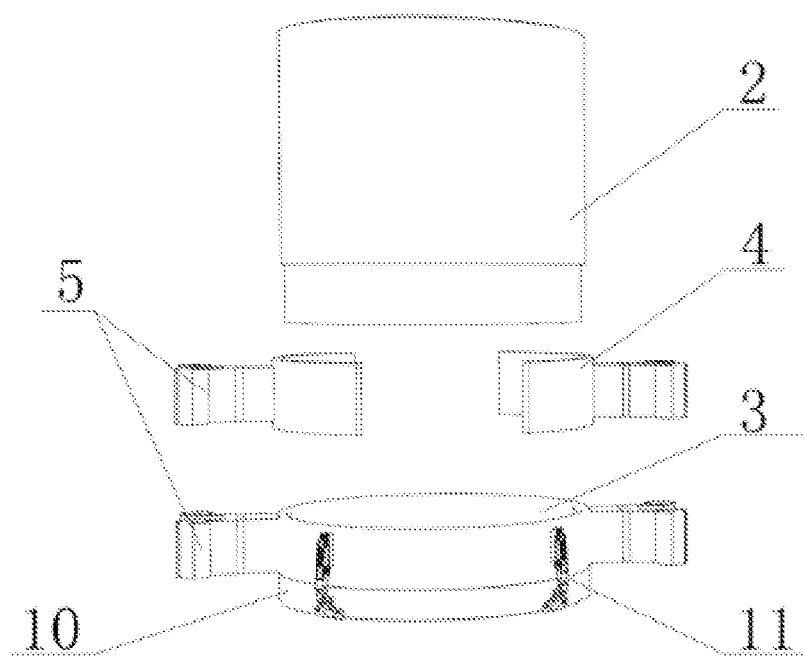
FIG. 3 is a structural diagram of a connector between the sample container and a truss according to the invention.

As shown in FIG. 2 and FIG. 3, the sample container comprises an inner container 1, an outer container 2, a top cover plate 14, a bottom cover plate 10 and a pile element 8. The inner container 1 is a cylindrical steel barrel, and in this embodiment, the inner container 1 has an inner diameter of 1 m, a height of 1 m and a wall thickness of 1 cm. The inner container 1 contains a rock-soil sample and can be used as a rock-soil sampler to carry out field sampling together with a self-made sampler, such that disturbance to the sample can be reduced. The outer container 2 is a special-shaped steel barrel with the size of the outer surface of an upper portion being greater than the size of the outer surface of a lower portion, and the inner container 1 is located in the outer container 2. In this embodiment, the outer container 2 has an inner diameter of 1.01 m and a height of 1 m, the upper portion of the outer container has a height of 0.8 m and an outer diameter of 1.03 m, the lower portion of the outer container has a height of 0.2 m and an outer diameter of 1.02 m, the diameter of the lower portion of the outer container is 0.01 m smaller than the diameter of the upper portion of the outer container, a step is formed by the variation of the outer diameter of the outer container, and a fixing ring for connecting the truss and the sample container is exactly clamped on the step, so that the sample container is suspended and fixed on the truss.

The outer container 2 and the truss are connected through fixing rings and truss gusset plates 5. The middle of the outer container 2 is connected to the truss supports 16 through fixing rings II 4 and the truss gusset plates 5, the two fixing rings II 4 are symmetrically arranged in the middle of the outer surface of the outer container 2, one end of each fixing ring II 4 is formed with an arc opening which clamps the outer surface of the outer container 2, the other end of each fixing ring II 4 is fixedly connected to one truss gusset plate 5, and the other end of each truss gusset plate 5 is connected to one truss support 16. Through the fixing rings II 4 on two sides, the outer container 2 is clamped and fixed, and the sample container is suspended and fixed on the truss supports 16, such that the sample container can be prevented from shaking leftwards or rightwards in the loading process of the pile element, which may otherwise affect test results.

The truss gusset plates 5 are disposed around the truss supports 16, and the positions of the truss gusset plates 5 on the truss supports 16 can be adjusted, so that the sample container can be adjusted to a proper height to facilitate loading and unloading of a soil sample. A fixing ring I 3 is arranged on the step formed by the variation of the outer diameter of the outer container 2, is clamped on a lower portion of the outer surface of the outer container 2, and is circular and closed, two truss gusset plates 5 are symmetrically arranged on the outer side of the fixing ring I 3, the lower portion of the outer container 2 is connected to the truss supports 16 through the fixing ring I 3 and the truss gusset plates 5. One end of each truss gusset plate 5 is connected to one truss support 16, and the other end of each truss gusset plate 5 is fixedly connected to the fixing ring I 3. Through the fixing ring I 3 on two sides, the outer container 2 is clamped and fixed, and the sample container is suspended and fixed on the truss supports 16.

Figure 4:
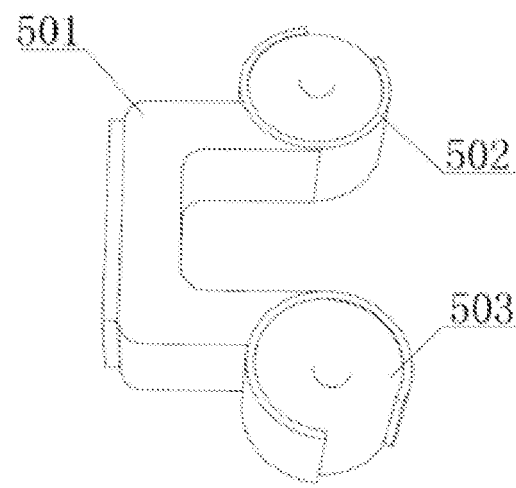
FIG. 4 is a structural diagram of a truss gusset plate according to the invention.

As shown in FIG. 4, each truss gusset plate 5 comprises a connecting plate 501, connecting rings 502 and fixing sleeves 503, wherein two ends of the connecting plate 501 are fixedly connected to the connecting rings 502, respectively, the connecting rings 502 are cylindrical, and the fixing sleeves 503 are fixed in the connecting rings 502. The connecting plate 501 is fixedly connected to the fixing rings, the fixing sleeves 503 are disposed around the outer surfaces of the truss supports 16, bolts are arranged in the connecting rings 502 and the fixing sleeves 503, and the fixing sleeves 503 can be fixedly connected to the truss supports 16 by tightening the bolts. When the positions of the truss gusset plates 5 need to be adjusted, the bolts are loosened to allow the truss gusset plates 5 to move vertically along the truss supports 16, and the fixing sleeves 503 have a guide effect in the moving process. The fixing rings are supported and fixed by the truss gusset plates 5.

The top cover plate 14 is arranged at the top of the sample container, and the bottom cover plate 10 is arranged at the bottom of the sample container, wherein the top cover plate 14 is fixedly connected with the servo consolidation mechanism, the bottom cover plate 10 is located below the fixing ring and is fixedly connected to the fixing ring I 3 through spring latches 11 arranged at intervals in an axial direction of the fixing ring I 3, upper ends of the spring latches 11 are fixedly connected to the fixing ring I 3, and lower ends of the spring latches 11 are fixedly connected to the bottom cover plate 10.

Porous filter plates 6 are arranged above and below the rock-soil sample in the inner container 1, respectively. Porous filter plates of different specifications can be used to simulate different drainage conditions so as to simulate different variations of the pore water pressure in a rock-soil body on the field. The pile element 8 penetrates through the center of the sample container and is inserted or implanted into the sample container via a pile pressing hole 18 formed in the center of the upper support plate 17, circular holes are formed in the center of the top cover plate 14, the center of each porous filter plate 6 and the center of the bottom cover plate 10 correspondingly to allow the pile element 8 to pass through, the diameter of the circular holes is slightly greater than that of the pile element 8 such that the pile element can be easily implanted in the sample container, and the pile element can move horizontally in all directions without being hindered in the test process. However, due to the existence of the circular holes, the rock-soil sample may be squeezed out via gaps between the porous filter plates and the pile element in the consolidation process and the loading process, so circular partition plates 9 are arranged between the porous filter plates 6 and the rock-soil sample and are disposed around the pile element 8, the inner diameter of the partition plates 9 is equal to the diameter of the pile element, and the outer diameter of the partition plates 9 is greater than the diameter of the circular holes in the centers of the porous filter plates, so that the rock-soil sample will not be squeezed out via the gaps between the pile element and the porous filter plates, and horizontal movement of the pile element in multiple directions will not be affected.

In the invention, the pile element 8 is a solid steel bar which is rigid enough, and considering the influence of the boundary effect, the diameter of the solid steel bar is set to 100 mm in this embodiment. The pile element 8 is directly pressed into the rock-soil sample in the sample container or is implanted into the rock-soil sample after a hole is drilled in a weathered rock, so as to simulate different pile sinking conditions. To ensure close contact between the pile element 8 and soil/rock, loading will not be carried out until the pile element is stabilized for 24 hrs. An excess pore water pressure and soil pressure sensor is embedded in the surface of the pile element 8, displacement sensors are mounted at upper and lower ends of the pile element 8, and data acquired by the sensors are compared with data recorded by the multidirectional servo actuators to obtain a p-y curve by correction.

Figure 5:
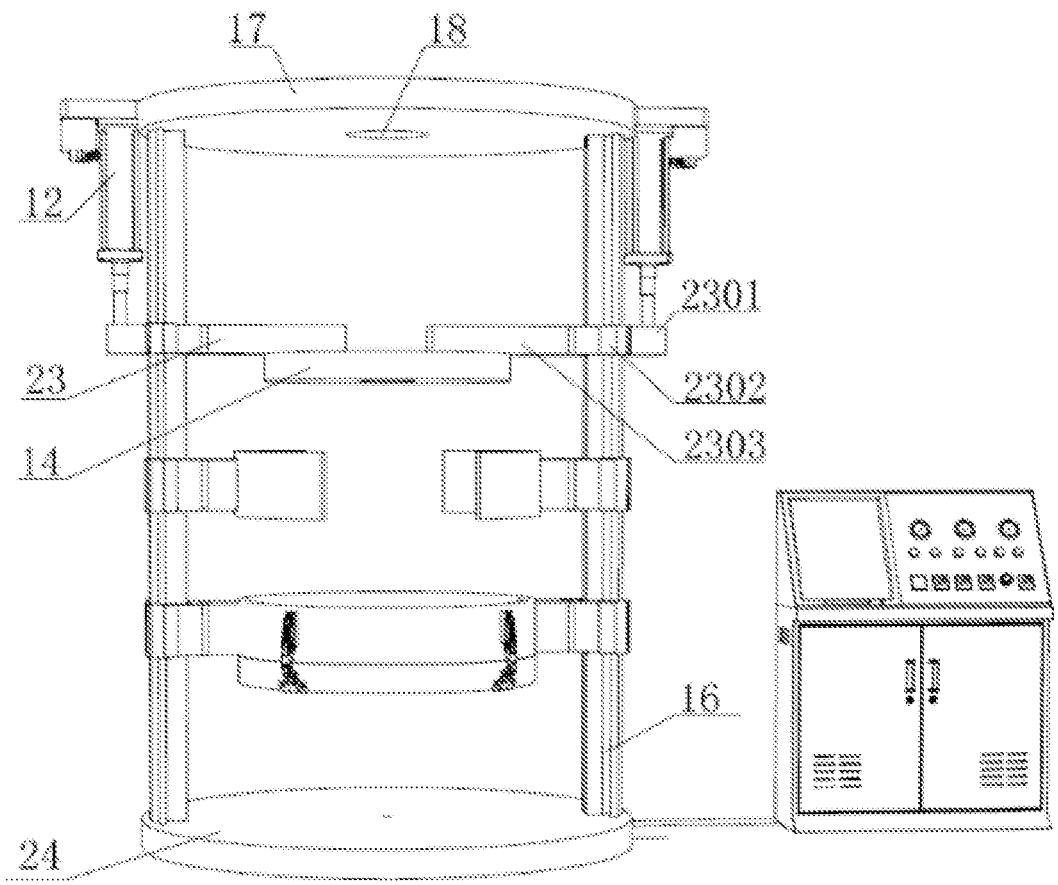
FIG. 5 is a connection diagram of a servo consolidation mechanism and the truss according to the invention.

In the invention, the servo consolidation mechanism is used to apply a vertical consolidation pressure to the top of the sample container. As shown in FIG. 5, the servo consolidation mechanism comprises two servo motors I 12 symmetrically arranged left and right and two pressure transmission sliders 23 fixedly connected to output ends of the servo motors I1 2, and top ends of the servo motors I 12 are fixedly connected to the upper support plate 17. Each pressure transmission slider 23 comprises a connecting block 2301, a truss gusset plate I 2302 and a pressing block 2303, wherein the truss gusset plate I 2302 is completely identical in structure with the truss gusset plates 5 and will not be detailed anymore herein. The connecting plates of the truss gusset plates I 2302 are fixedly connected to the pressing blocks 2303, the pressing blocks 2303 are strip-shaped steel blocks, and the top cover plate 14 is fixedly connected to bottom surfaces of the two pressing blocks 2303. The fixing sleeves of the truss gusset plates I 2302 are disposed around the truss supports, the connecting rings of the truss gusset plates I 2302 are fixedly connected to the connecting blocks 2301, and the connecting blocks 2301 are fixedly connected to the output ends of the servo motors I 12, so that the servo motors I 12 are connected to the pressure transmission sliders 23. When the servo motors I 12 work, the output ends of the servo motors I 12 drive the pressure transmission sliders 23 to slide vertically along the truss supports 16; when sliding vertically, the pressure transmission sliders 23 drive the top cover plate 14 to slide to transmit a pressure applied by the servo motors I 12 to the top cover plate 14; and when the top cover plate 14 makes contact with the rock-soil sample in the sample container, the pressure transmitted from the pressure transmission sliders 23 is uniformly applied to the rock-soil sample. In the invention, the pressure is controlled within 0-2 MPa to simulate the constant stress condition at different depths of the field, and a pressure sensor mounted on the porous filter plate 10 at the top of the rock-soil sample monitors the pressure in real time and feeds the monitored pressure back to a computer system of the computer console 15.

Figure 6:
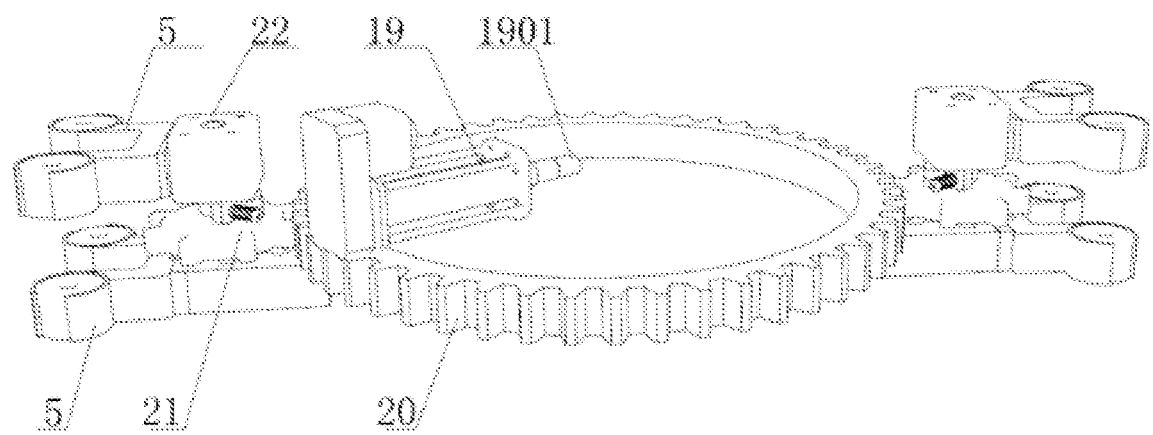
FIG. 6 is a structural diagram of a multidirectional servo actuator according to the invention.

In the invention, the multidirectional servo actuators are mounted at the top and the bottom of the pile element 8, respectively, and the two multidirectional servo actuators are controlled in parallel by the computer system. As shown in FIG. 6, each multidirectional servo actuator comprises a servo motor II 19, a gear disk 20 and two pinions 21 engaged with the gear disk 20 and arranged symmetrically, wherein the servo motor II 19 is fixed on the gear disk 20, and the two pinions 21 are both located on the outer side of the gear disk 20 and are in engaged transmission with the gear disk 20. The pinions 21 are arranged on support plates, central spindles of the pinions 21 are connected to output shafts of motors 22, and the motors 22 and the support plates are connected to the truss supports 16 through truss gusset plates 5. The multidirectional servo actuators are supported and fixed by the truss gusset plates 5, and the vertical positions of the multidirectional servo actuators can be adjusted through the truss gusset plates 5. In the invention, the computer system in the computer console 15 is connected to the motors 22 and controls the rotation of the motors 22 to control the rotation angle of the pinions 21, and thus, multidirectional rotation of the gear disks 20 and the servo motors II 19 is realized.

The multidirectional servo actuators can apply a monotonic load, a bidirectional horizontal cyclic load or a multi-degree-of-freedom cyclic load. When the gear disks 21 do not rotate, the two servo motors II 19 synchronously apply a load given by the computer system to the top and the bottom of the pile element, and at this moment, the multidirectional servo actuators apply the monotonic load. When a load is applied and released by the two servo motors II 9 in one direction, the computer system controls the pinions to rotate to drive the gear disks to rotate by 180°, then another load is applied and released again, that is, the servo motors II 19 applies cyclic loads both in a push direction and a pull direction, and at this moment, the multidirectional servo actuators apply the bidirectional horizontal cyclic load. After the servo motors II 19 apply a load in one direction to the pile element 8, the gear disks 21 are rotated to enable the servo motors II 19 to apply a load in another direction, the magnitude of the loads applied is determined as required by the test, and at this moment, the multidirectional servo actuators apply the multi-degree-of-freedom cyclic load.

The multidirectional servo actuators can realize real-time regular rotation of a load point in a given mode to enable the pile element 8 to move horizontally in one or more directions or to vibrate in different directions, such that dynamic load transmission along different loading paths is realized. The exciting force is converted from an input current of numerically-controlled motors, and a load-displacement time travel curve is recorded in real time to obtain p-y curves in different modes.

In the invention, the truss supports 16 are hollow pipe supports, and connecting lines between the computer system in the computer console 15 and the servo motors I 12, the servo motors II 19 and the motors 22 are arranged in hollow pipes of the truss supports 16.

The invention further provides a test method using the p-y curve-based element test device. The test method comprises the following steps:

First, carrying out field sampling: a rock-soil sample in the device can be acquired by field sampling, and the inner container is used as a rock-soil sampler to carry out field sampling together with a self-made sampler; after the sample is acquired, the inner container containing the rock-soil sample is placed back into the outer container, and then the truss gusset plates 5 are adjusted to fix the sample container to a proper height;

Second, applying a vertical consolidation pressure: after the rock-soil sample is contained in the sample container, the computer system controls the servo consolidation mechanism to apply a required vertical consolidation pressure downwards, and the pressure sensor mounted at the top of the soil sample monitors the pressure in real time and feeds the monitored pressure back to the computer system;

Third, implanting a pile element: the rock-soil sample is consolidated for 2-3 days according to the soil characteristics, and when the stress condition of a soil body becomes stable, the pile element 8 is directly pressed into the rock-soil sample via the pile pressing hole or is implanted into the rock-soil sample by means of mechanical drilling; and Fourth, carrying out cyclic loading on the pile element: after the pile element 8 is implanted, the consolidation pressure is maintained and stabilized for 24 hrs, then the computer system controls the multidirectional servo actuators to carry out cyclic loading and acquire the pressure, load and displacement of the rock-soil sample in real time, and data are collated to obtain a p-y curve.

The p-y curve-based element test device and the test method provided by the invention have been introduced in detail above. Several specific embodiments are used in this specification to expound the principle and implementation of the invention, and the description of the above embodiments is merely used for assisting users in understanding the method and key concept of the invention. It should be noted that those ordinarily skilled in the art can make different improvements and modifications without departing from the principle of the invention, and all these improvements and modifications also fall within the protection scope of the claims of the invention. Those skilled in the art can implement or use the invention with reference to the description of the embodiments disclosed above. Different alterations of these embodiments will be obvious to those skilled in the field. The general principle defined in this specification can be implemented in other embodiments without departing from the spirit or scope of the invention. Thus, the invention will not be limited to these embodiments illustrated in this specification and should have a broadest scope in conformity with the principle and novelty disclosed in this specification.

What is claimed is:

1. A p-y curve-based element test device, comprising
a truss,
a sample container,
a servo consolidation mechanism, and
multidirectional servo actuators;
wherein
the truss comprises an upper support plate, a lower support plate and truss supports,
the upper support plate is located above the lower support plate and the upper support plate is fixedly connected to the lower support plate through the truss supports symmetrically arranged on a left side and a right side,
at least one truss support is arranged on each of the left side and the right side,
the sample container, the servo consolidation mechanism and the multidirectional servo actuators are respectively connected to the truss supports on the left side and the right side,
the servo consolidation mechanism is located above the sample container, and the multidirectional servo actuators are arranged above the servo consolidation mechanism and below the sample container, respectively;
the sample container comprises an inner container, an outer container, a top cover plate, a bottom cover plate and a pile element, wherein
the inner container contains a rock-soil sample and the inner container is located in the outer container,
the outer container is connected to the truss through a first fixing ring, two second fixing rings and four first truss gusset plates,
the top cover plate is arranged at a top of the sample container,
the bottom cover plate is arranged at a bottom of the sample container,
the top cover plate is fixedly connected to the servo consolidation mechanism,
the bottom cover plate is located below the first fixing ring and the two second fixing rings, and the bottom cover plate is fixedly connected to the first fixing ring through a plurality of spring latches;
porous filter plates are arranged above and below the rock-soil sample in the inner container,
the pile element penetrates through a center of the sample container,
circular holes are formed in a center of the top cover plate, a center of each porous filter plate of the porous filter plates and a center of the bottom cover plate correspondingly,
a diameter of the circular holes is greater than a diameter of the pile element,
partition plates are arranged between the porous filter plates and the rock-soil sample and the partition plates are disposed around the pile element, and an outer diameter of the partition plates is greater than the diameter of the circular hole in the center of the porous filter plates;
the servo consolidation mechanism comprises two first servo motors symmetrically arranged left and right and two pressure transmission sliders fixedly connected to output ends of the two first servo motors,
top ends of the two first servo motors are fixedly connected to the upper support plate,
first ends of the two pressure transmission sliders are fixedly connected to bottoms of the two first servo motors,
bottoms of second ends of the two pressure transmission sliders are fixedly connected to the top cover plate, and the two pressure transmission sliders are disposed around the truss supports;
the multidirectional servo actuators are mounted at a top and a bottom of the pile element, respectively, and each multidirectional servo actuator of the multidirectional servo actuators comprises a second servo motor, a gear disk and two pinions engaged with the gear disk and arranged symmetrically, wherein
the second servo motor is fixed on the gear disk,
the two pinions are located on an outer side of the gear disk and the two pinions are arranged on support plates, respectively,
central spindles of the two pinions are connected to output shafts of motors, and
the motors and the support plates are connected to the truss supports through two second truss gusset plates, respectively.

2. The p-y curve-based element test device according to claim 1, wherein
each first truss gusset plate of the two first truss gusset plates comprises a connecting plate, connecting rings and fixing sleeves, wherein
two ends of the connecting plate are fixedly connected to the connecting rings, respectively,
the connecting rings are cylindrical, the fixing sleeves are fixed in the connecting rings,
the connecting plate is fixedly connected to the first fixing ring, the two second fixing rings, the motors, and the support plates, respectively, and
the fixing sleeves are disposed around outer surfaces of the truss supports and the fixing sleeves are fixedly connected to the truss supports by tightening bolts.

3. The p-y curve-based element test device according to claim 2, wherein
each of the two pressure transmission sliders comprises a connecting block, third truss gusset plates and a pressing block,
connecting plates of the third truss gusset plates are fixedly connected to the pressing blocks,
the pressing blocks are strip-shaped steel blocks,
the top cover plate is fixedly connected to bottom surfaces of the two pressing blocks,
fixing sleeves of the third truss gusset plates are fixedly disposed around the truss supports,
connecting rings of the third truss gusset plates are fixedly connected to the connecting blocks, and
the connecting blocks are fixedly connected to the output ends of the two first servo motors.

4. The p-y curve-based element test device according to claim 1, wherein
the inner container is a cylindrical barrel,
the outer container is a special-shaped barrel with an upper portion and a lower portion, wherein a size of an outer surface of the upper portion is greater than a size of an outer surface of the lower portion, and a step is formed by a variation of an outer diameter of the outer container;
a middle of the outer container is connected to the truss supports through the two second fixing rings and two of the four first truss gusset plates,
the two second fixing rings are symmetrically arranged in a middle of an outer surface of the outer container, and each second fixing ring of the two second fixing rings has a first end formed with an arc opening and a second end fixedly connected to one of the four first truss gusset plates, wherein the arc opening clamps the outer surface of the outer container;
the first fixing ring is arranged on the step formed by the variation of the outer diameter of the outer container,
the first fixing ring is clamped on a lower portion of the outer surface of the outer container, and the first fixing ring is circular and closed,
the two of the four first truss gusset plates are symmetrically arranged on an outer side of the first fixing ring, and the first fixing ring is fixedly connected to the two of the four first truss gusset plates;
the two of the four first truss gusset plates are disposed around the truss supports, and
positions of the two of the four first truss gusset plates on the truss supports are adjustable.

5. The p-y curve-based element test device according to claim 1, further comprising
a computer console, wherein a computer system is installed in the computer console and the computer system is connected to the two first servo motors, the two second servo motors and the motors.

6. The p-y curve-based element test device according to claim 5, wherein
the truss supports are hollow pipe supports, and connecting lines between the computer system and the two first servo motors, the two second servo motors and the motors are arranged in hollow pipes of the truss supports.

7. A test method using the p-y curve-based element test device according to claim 5, comprising:
S1: carrying out field sampling, wherein the inner container is used as a rock-soil sampler to carry out the field sampling together with a self-made sampler; after the field sampling is finished, the inner container containing the rock-soil sample is placed back into the outer container; a height of the sample container is adjusted, and then the sample container is fixed;
S2: applying a vertical consolidation pressure, wherein the computer system controls the servo consolidation mechanism to apply a predetermined vertical consolidation pressure downwards, a pressure sensor mounted at a top of the rock-soil sample monitors the predetermined vertical consolidation pressure in real time and feeds a monitored pressure back to the computer system;
S3: implanting the pile element, wherein the rock-soil sample is consolidated for 2-3 days, and when a stress condition of a soil body becomes stable, the pile element is directly pressed into the rock-soil sample via a pile pressing hole or the pile element is implanted into the rock-soil sample by mechanical drilling; and
S4: carrying out cyclic loading on the pile element, wherein after the pile element is implanted, the predetermined vertical consolidation pressure is maintained and stabilized for 24 hrs, then the computer system controls the multidirectional servo actuators to carry out the cyclic loading, and a load-displacement time travel curve is recorded in real time to obtain a p-y curve.

8. The test method according to claim 7, wherein
the multidirectional servo actuators apply a monotonic load, a bidirectional horizontal cyclic load or a multi-degree-of-freedom cyclic load;
when the gear disks do not rotate, the two second servo motors synchronously apply a load given by the computer system to the top and the bottom of the pile element, and the multidirectional servo actuators apply the monotonic load;
when a first load is applied and released by the two second servo motors in a first direction, the computer system controls the pinions to rotate to drive the gear disks to rotate by 180°, then a second load is applied and released again, and the multidirectional servo actuators apply the bidirectional horizontal cyclic load; and
after the two second servo motors apply the first load in the first direction to the pile element, the gear disks are rotated to enable the two second servo motors to apply a second load in a second direction, and the multidirectional servo actuators apply the multi-degree-of-freedom cyclic load.

9. The test method according to claim 7, wherein
the truss supports are hollow pipe supports, and
connecting lines between the computer system and the two first servo motors, the two second servo motors and the motors are arranged in hollow pipes of the truss supports.

* * * * *